United States Patent
Li et al.

(10) Patent No.: US 12,427,129 B2
(45) Date of Patent: Sep. 30, 2025

(54) APPLICATION OF COMPOUND AMINO ACIDS IN PREPARATION OF MEDICAMENT FOR IMPROVING SENSITIVITY OF BACTERIA TO ANTIBIOTICS

(71) Applicant: SUN YAT-SEN UNIVERSITY, Guangdong (CN)

(72) Inventors: Hui Li, Guangdong (CN); Bo Peng, Guangdong (CN); Xuanxian Peng, Guangdong (CN); Shishi Lai, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 754 days.

(21) Appl. No.: 17/787,592

(22) PCT Filed: Jul. 20, 2021

(86) PCT No.: PCT/CN2021/107306
§ 371 (c)(1),
(2) Date: Jun. 21, 2022

(87) PCT Pub. No.: WO2022/028243
PCT Pub. Date: Feb. 10, 2022

(65) Prior Publication Data
US 2022/0409563 A1    Dec. 29, 2022

(30) Foreign Application Priority Data

Aug. 6, 2020   (CN) .......................... 202010781673.0

(51) Int. Cl.
| | | |
|---|---|---|
| *A61K 45/06* | (2006.01) |
| *A61K 31/198* | (2006.01) |
| *A61K 31/401* | (2006.01) |
| *A61K 31/405* | (2006.01) |
| *A61K 31/407* | (2006.01) |
| *A61K 31/4172* | (2006.01) |
| *A61K 31/43* | (2006.01) |
| *A61K 31/4709* | (2006.01) |
| *A61K 31/546* | (2006.01) |
| *A61K 31/7036* | (2006.01) |
| *A61P 31/04* | (2006.01) |

(52) U.S. Cl.
CPC .......... *A61K 31/198* (2013.01); *A61K 31/401* (2013.01); *A61K 31/405* (2013.01); *A61K 31/407* (2013.01); *A61K 31/4172* (2013.01); *A61K 31/43* (2013.01); *A61K 31/4709* (2013.01); *A61K 31/546* (2013.01); *A61K 31/7036* (2013.01); *A61P 31/04* (2018.01)

(58) Field of Classification Search
CPC .. A61K 31/198; A61K 31/401; A61K 31/405; A61K 31/4172; A61K 31/4709; A61K 31/546; A61K 31/7036; A61P 31/04
See application file for complete search history.

(56) References Cited

FOREIGN PATENT DOCUMENTS

| | | |
|---|---|---|
| CN | 102871996 | 1/2013 |
| CN | 107308453 | 11/2017 |
| CN | 107737338 | 2/2018 |
| CN | 108042521 | 5/2018 |
| CN | 111744016 | 10/2020 |

OTHER PUBLICATIONS

CN107308453 English Translation; pp. 1-17 (2017) (Year: 2017).*
CN107737338A English translation, pp. 1-19 (Feb. 2018) (Year: 2018).*
CN108042521 English translation, pp. 1-14 (May 2018) (Year: 2018).*
"International Search Report (Form PCT/ISA/210) of PCT/CN2021/107306", mailed on Oct. 15, 2021, with English translation thereof, pp. 1-6.
Jin-Zhou Ye et al., "Identification and efficacy of glycine, serine and threonine metabolism in potentiating kanamycin-mediated killing of Edwardsiella piscicida," Journal of Proteomics, vol. 183, May 2018, pp. 1-42.

* cited by examiner

*Primary Examiner* — Julie Ha
*Assistant Examiner* — Kristina M Hellman
(74) *Attorney, Agent, or Firm* — JCIPRNET

(57) ABSTRACT

The invention belongs to the technical field of biomedicament, and more specifically relates to an application of compound amino acids in preparation of a medicament for improving sensitivity of bacteria to antibiotics. Experiments have shown that a combination of compound amino acids and antibiotics can improve the sensitivity of bacteria to antibiotics, promote an entry of antibiotics into bacterial cells, significantly increase an intracellular antibiotic content, and improve a bactericidal effect of antibiotics, thereby reducing a survival rate of bacteria, and treating diseases caused by bacterial infection.

4 Claims, 18 Drawing Sheets

APPLICATION OF COMPOUND AMINO ACIDS IN PREPARATION OF MEDICAMENT FOR IMPROVING SENSITIVITY OF BACTERIA TO ANTIBIOTICS

This is a 371 application of the International PCT application serial no. PCT/CN2021/107306, filed on Jul. 20, 2021, which claims the priority benefits of China Application No. 202010781673.0, filed on Aug. 6, 2020. The entirety of each of the above-mentioned patent applications is hereby incorporated by reference herein and made a part of this specification.

TECHNICAL FIELD

The invention belongs to the technical field of biomedicament, and more specifically relates to an application of compound amino acids in preparation of a medicament for improving sensitivity of bacteria to antibiotics.

DESCRIPTION OF RELATED ART

In the early twentieth century, discovery and application of antibiotics brought bacterial infections under control. However, with an emergence of resistant bacteria and superbugs, antibiotics are less effective or even ineffective in treating bacterial diseases, and human beings are facing new challenges. At present, speed at which bacteria develop drug resistance is gradually accelerating, and difficulty and time of new drug research and development are gradually increasing. If this continues, there may be a dangerous situation in which no medicaments are available in the near future, seriously threatening human health and life safety.

Amino acids, as small molecular compounds that widely exist in nature, are important substances that promote human growth, maintain normal body metabolism, and provide life activities, and are also raw materials for synthesizing antibodies, hormones, enzymes and other tissues needed by the body, and basic units that constitute human proteins. Existing research has found that a combination of some amino acids with antibiotics can improve the sensitivity of bacteria to antibiotics. For example, Chinese patent application CN107308453A discloses a new application of cystine or cysteine, that is combining cystine or cysteine with antibiotics can improve sensitivity of bacteria to antibiotics and improve a bactericidal effect of antibiotics, but the effect achieved is limited, and it is aimed at sensitive bacteria such as *Escherichia coli* and *Staphylococcus*, and for bacteria that have developed drug resistance, the effect of combining single amino acid with antibiotics needs to be improved.

SUMMARY

The technical problem to be solved by the present invention is to overcome the limited effect of combining single amino acid with antibiotics to improve sensitivity of bacteria to antibiotics, and especially defects and deficiencies of unsatisfactory effects for bacteria that have developed drug resistance, and explore a new solution for improving the sensitivity of bacteria to antibiotics.

Another objective of the present invention is to provide an application of compound amino acids in preparation of a medicament for improving sensitivity of bacteria to antibiotics.

The above-mentioned objectives of the present invention are achieved through the following technical solutions.

Our previous studies have shown that alanine, glutamine, and L-aspartic acid have an effect of improving sensitivity of bacteria to antibiotics, however not all amino acids have this effect, and at the same time, after various amino acids act on the body, a mechanism of action to improve the sensitivity of bacteria to antibiotics is different. Therefore, it is unpredictable whether an ability to greatly improve the sensitivity of bacteria to antibiotics can be achieved by compounding of multiple amino acids. After a lot of exploration and researches, a combination of compound amino acids is formed, which can significantly improve the sensitivity of bacteria to antibiotics, promote an entry of antibiotics into bacterial cells, significantly increase an intracellular antibiotic content, and improve a bactericidal effect of antibiotics, thereby reducing a survival rate of bacteria, and treating diseases caused by bacterial infection, and when a preparation of compound amino acids is applied to preparation of a medicament for improving sensitivity of bacteria to antibiotics, there is an excellent effect.

Therefore, it is provided in the present invention an application of compound amino acids in preparation of a medicament for improving sensitivity of bacteria to antibiotics.

Further, a total amino acid content of the compound amino acids is 5%-12%. Preferably, the total amino acid content of the compound amino acids is 5%-8%; more preferably, the total amino acid content of the compound amino acids is 5%.

Even further, the compound amino acids contain glycine, serine, tryptophan, lysine and threonine.

Preferably, the compound amino acids contain aspartic acid, glutamic acid, serine, histidine, glycine, threonine, alanine, arginine, tyrosine, cystine, valine, methionine, tryptophan, phenylalanine, isoleucine, leucine, lysine acetate, and proline.

Further, in the compound amino acids, a molar concentration ratio of each amino acid to total amino acids is: aspartic acid 2.65%-2.8%, glutamic acid 4.09%-4.23%, serine 2.37%-4.64%, histidine 4.62%-4.81% %, glycine 11.25%-11.6%, threonine 5.06%-5.22%, alanine 19.57%-20.11%, arginine 6.88%-7%, tyrosine 0.16%-0.27%, cystine 0.09%-0.21%, valine 6.67%-6.8%, methionine 4.04%-4.17%, tryptophan 0.98%-1.04%, phenylalanine 5.12%-5.27%, isoleucine 4.59%-4.74%, leucine 6.44%-6.45%, lysine acetate 6.59%-6.64% and proline 6.23%-6.32%.

The compound amino acids may further contain a pharmaceutically acceptable excipient, to be made into a dosage form such as an oral solution and an injection.

Even further, the antibiotics include β-lactam antibiotics, quinolone antibiotics (balofloxacin) and aminoglycoside antibiotics (gentamicin).

Wherein, β-lactam antibiotics include cephalosporin antibiotics (cefazolin, ceftriaxone, ceftiofur), penicillin antibiotics (ampicillin) and carbapenem antibiotics (imipenem, meropenem, ertapenem).

Further, the bacteria include sensitive bacteria and resistant bacteria.

Even further, the bacteria include Gram-positive bacteria and Gram-negative bacteria.

Wherein, the Gram-negative bacteria include *Escherichia coli, Vibrio alginolyticus, Vibrio parahaemolyticus*, and *Pseudomonas aeruginosa*; the Gram-positive bacteria include *Bacillus subtilis, Staphylococcus, Streptococcus, Diplococcus pneumoniae, Bacillus anthracia*, and *Bacillus tetani*.

In addition, it is further provided in the present invention a medicament for improving sensitivity of bacteria to antibiotics, which contains an effective amount of compound amino acids and antibiotics.

Further, a mass ratio of antibiotics to total amino acids in the compound amino acids is 1:12.5 to 1:1824.

It is provided a medicament for improving sensitivity of bacteria to antibiotics, including 5%-12% of compound amino acids, 0.01-4 mg/mL antibiotics, and water as the rest. The medicament for improving sensitivity of bacteria to antibiotics may further include an appropriate amount of a pharmaceutically acceptable excipient, to be prepared into a preparation such as an oral solution and an injection.

The present invention has the following beneficial effects.

The present invention discloses for the first time an application of compound amino acids in preparation of a medicament for improving sensitivity of bacteria to antibiotics, combining compound amino acids with antibiotics significantly can improve sensitivity of bacteria to antibiotics, promotes an entry of antibiotics into bacterial cells, significantly increases an intracellular antibiotic content, and improves a bactericidal effect of antibiotics, thereby reducing a survival rate of bacteria, and treating diseases caused by bacterial infection.

At the same time, based on the solution of the present invention, the existing preparation products of compound amino acids can be directly used, which are prepared from a variety of amino acids, carbohydrates, electrolytes, trace elements, vitamins and pH adjusters, etc., with high purity and low nitrogen content, few adverse reactions and other advantage that almost all can be used for protein synthesis, as a basic nitrogen supply for parenteral nutrition. At present, compound amino acids are mainly used as supplementary nutritional preparations in clinical practice, which have passed clinical trials and are safe and reliable.

DESCRIPTION OF THE EMBODIMENTS

The present invention is further described below with reference to accompanying drawings and specific embodiments, but the embodiments do not limit the present invention in any form. Unless otherwise specified, reagents, methods and equipment used in the present invention are conventional reagents, methods and equipment in the technical field.

Unless otherwise specified, the reagents and materials used in the following embodiments are commercially available.

Figure 1:
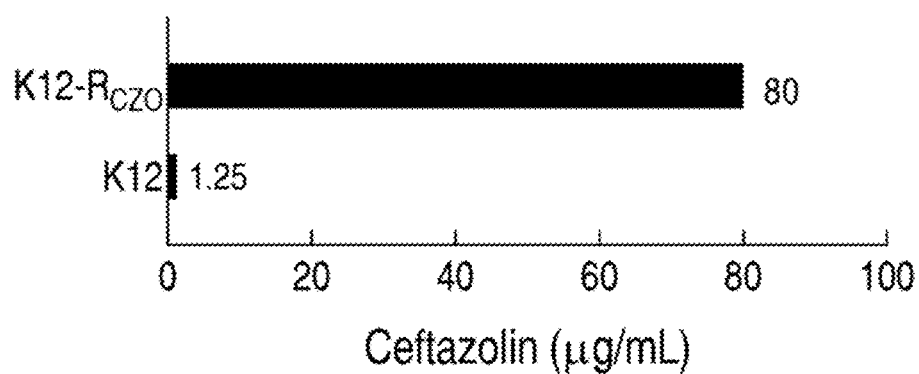
FIG. 1 is a result statistical graph of measurements of minimum inhibitory concentration (MIC) of *Escherichia coli* resistant bacteria obtained by artificial passage against cefazolin in Embodiment 1.

Embodiment 1 Improvement of Compound Amino Acids on Sensitivity of *Escherichia coli* Cefazolin-Resistant Bacteria to Cefazolin 1.1 Acquisition of Artificially Passaged Resistant Bacteria—*Escherichia coli* Cefazolin-Resistant Bacteria Taking *Escherichia coli* sensitive bacteria K12 as starting strain, it was serially passaged in a liquid medium containing cefazolin with ½ of minimum inhibitory concentration (MIC), streaked on a plate every five passages, and single clone was obtained and determined its MIC against cefazolin; until MIC of the obtained strain is 80 μg/mL, which is 64 times that of the starting strain (see FIG. 1 for details), it is named as *Escherichia coli* cefazolin-resistant bacteria (K12-R$_{CZO}$).

1.2 Improvement of Compound Amino Acids on Sensitivity of *Escherichia coli* Sensitive Bacteria and *Escherichia coli* Cefazolin-Resistant Bacteria to Cefazolin Experimental materials: three kinds of compound amino acids with a total amino acid content of 5%, 8.5%, and 11.4%, respectively. A molar concentration ratio of each amino acid to total amino acids in the three kinds of compound amino acids is shown in Table 1.

TABLE 1 molar concentration ratio of each amino acid to total amino acids in three kinds of compound amino acids

| Amino acid | 5% compound amino acids | 8.5% compound amino acids | 11.4% compound amino acids |
|---|---|---|---|
| Aspartic acid | 2.80% | 2.69% | 2.65% |
| Glutamic acid | 4.23% | 4.09% | 4.14% |
| Serine | 2.37% | 4.64% | 4.58% |
| Histidine | 4.81% | 4.62% | 4.69% |
| Glycine | 11.60% | 11.27% | 11.25% |
| Threonine | 5.22% | 5.06% | 5.12% |
| Alanine | 20.11% | 19.65% | 19.57% |
| Arginine | 7.00% | 6.92% | 6.88% |
| Tyrosine | 0.27% | 0.16% | 0.18% |
| Cystine | 0.21% | 0.12% | 0.09% |
| Valine | 6.80% | 6.74% | 6.67% |
| Methionine | 4.17% | 4.04% | 4.09% |
| Tryptophan | 1.04% | 0.98% | 1.00% |
| Phenylalanine | 5.27% | 5.12% | 5.12% |
| Isoleucine | 4.74% | 4.59% | 4.65% |
| Leucine | 6.45% | 6.45% | 6.44% |
| Lysine acetate | 6.64% | 6.61% | 6.59% |
| Proline | 6.27% | 6.23% | 6.32% |

Test Subject:

Preparation of bacterial samples: monoclonal bacteria of sensitive bacteria K12 or resistant bacteria K12-R$_{CZO}$ were picked and inoculated in 50 mL LB liquid medium respectively. After incubation for 17 h at 37° C. and 200 rpm, bacterial cells were collected by centrifugation at 8000 rpm for 4 min; the bacterial cells were washed twice with 0.85% normal saline, suspended in 1×M9 medium, adjusted to OD600 as 0.6, and then dispensed 5 mL into test tubes for subsequent experimental research.

Figure 2:
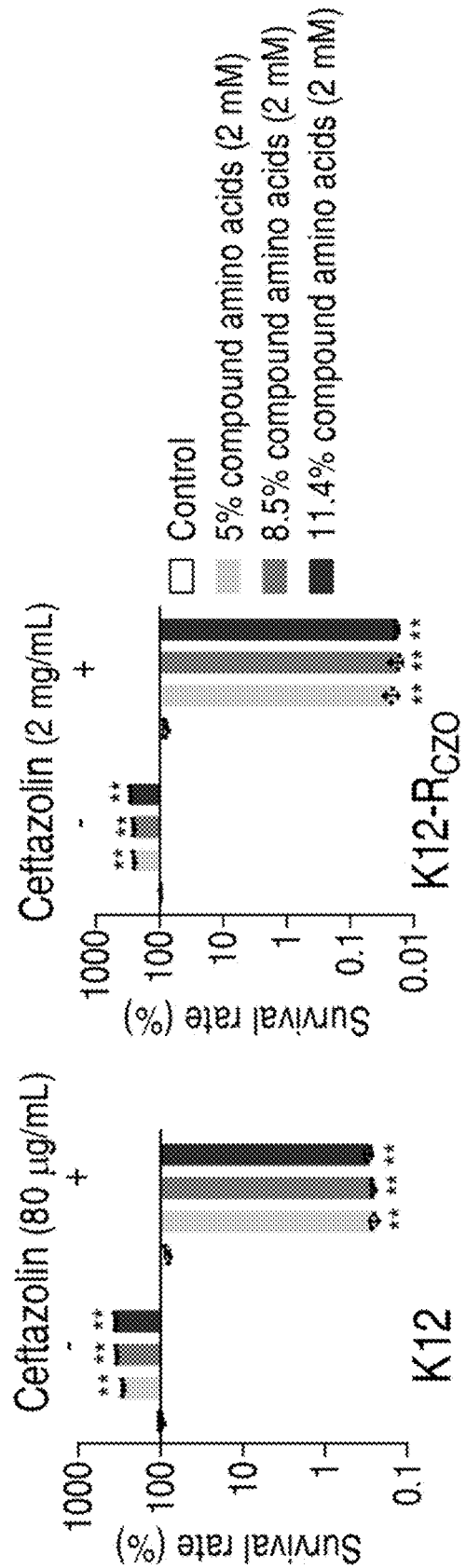
FIG. 2 is a result statistical graph of survival rates of *Escherichia coli* sensitive bacteria and *Escherichia coli* resistant bacteria against three compound amino acids in synergy with cefazolin in Embodiment 1.

1.2.1 Improvement of Compound Amino Acids on Sensitivity of Sensitive Bacteria K12 and Resistant Bacteria K12-R$_{CZO}$ to Cefazolin Compound amino acids with a total amino acid content of 5%, 8.5%, and 11.4% were prepared into a solution with a final total amino acid molar concentration of 2 mM, which acted on bacteria for 6 hours in synergy with cefazolin (a concentration being 80 μg/mL for sensitive bacteria, and a concentration being 2 mg/mL for resistant bacteria), 100 μL was taken for doubling dilution, and 10 μL of bacterial solution was taken for plate count; data that colonies are in a range of 20 to 200 can be used for statistical analysis, and a survival rate of bacteria is a percentage of bacterial CFU (colony forming units/ml) in treatment group to bacterial CFU in control group, with 3 biological replicates for each treatment; results are shown in FIG. 2.

It can be seen from the figure that a survival rate of sensitive bacteria K12 when applied with 5%, 8.5% and 11.4% of compound amino acids in synergy with cefazolin is reduced by 320 times, 310 times and 274 times, respectively; a survival rate of resistant bacteria K12-R$_{CZO}$ is reduced by 3,556 times, 4,299 times and 4,273 times, respectively. It shows that the compound amino acids of three ratios all can effectively restore sensitivity of bacteria to cefazolin, and there is no significant difference in the synergistic bactericidal effect among the three. Therefore, follow-up experiments were conducted using 5% compound amino acids with the lowest concentration ratio.

Figure 3:
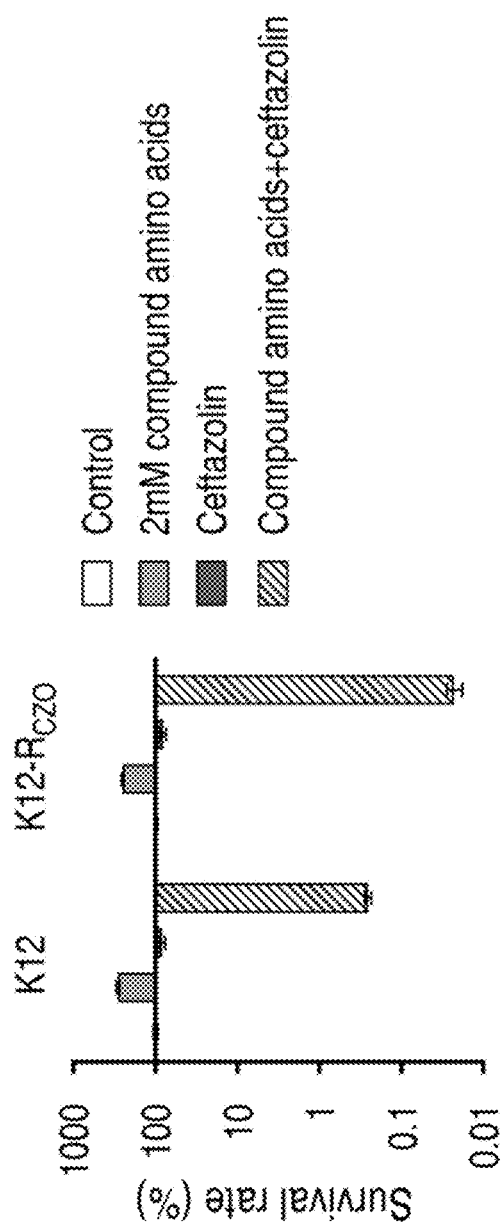
FIG. 3 is a result statistical graph of experiments of compound amino acids improving sensitivity of sensitive bacteria K12 and resistant bacteria K12-$R_{CZO}$ to cefazolin in Embodiment 1.

1.2.2 Improvement of 5% Compound Amino Acids on Sensitivity of Sensitive Bacteria K12 and Resistant Bacteria K12-R$_{CZO}$ to Cefazolin Each of prepared bacterial samples was divided into 4 groups: control group, group of 2 mM 5% compound amino acids added only, and group of cefazolin antibiotics added only (a concentration being 80 μg/mL for sensitive bacteria K12, and a concentration being 2 mg/mL for resistant bacteria K12-R$_{CZO}$), and group of cefazolin and 2 mM compound amino acids added. Bacteria were incubated at 37° C. and 200 rpm for 6 h, and then 100 μL was taken for doubling dilution, and 10 μL of bacterial solution was taken therefrom for plate count to calculate a survival rate of bacteria; results are shown in FIG. 3.

It can be seen from the figure that a survival rate of sensitive bacteria K12 when applied with compound amino acids in synergy with cefazolin is reduced by 320 times; a survival rate of resistant bacteria K12-R$_{CZO}$ is reduced by 3,556 times. It shows that compound amino acids can improve sensitivity of bacteria, including artificially passaged resistant bacteria, to cefazoline.

Figure 4:
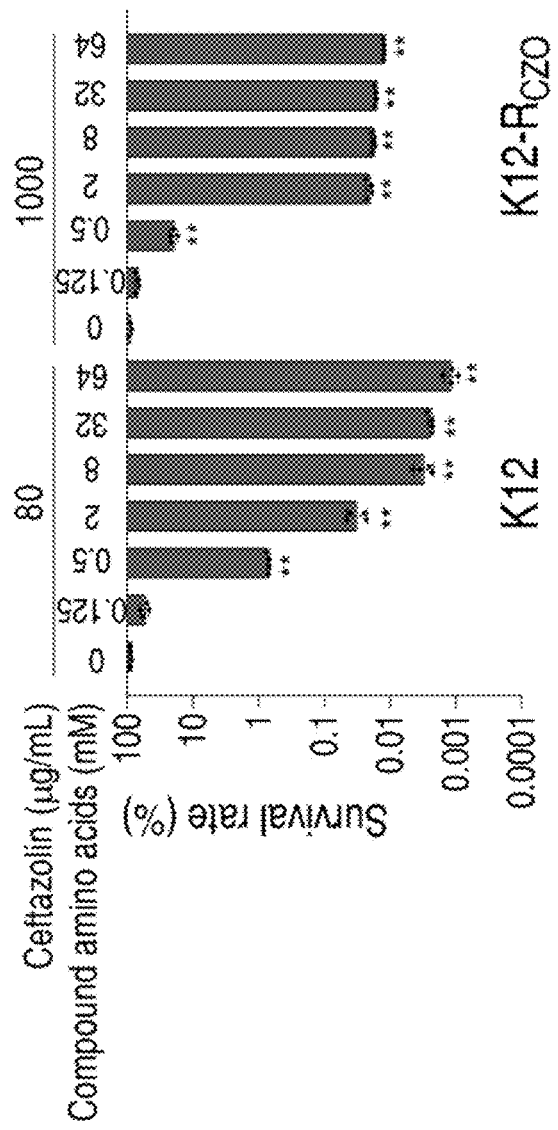
FIG. 4 is a result statistical graph of effects of compound amino acids with different concentration gradients on improving sensitivity of *Escherichia coli* to cefazolin in Embodiment 1.

1.2.3 Study on Important Conditions for Compound Amino Acids to Improve Sensitivity of Cefazolin-Resistant Bacteria to Cefazolin 1.2.3.1 Concentration Dependency About Compound Amino Acids Improving Sensitivity of *Escherichia coli* to Cefazolin In order to understand whether there is a gradient effect between a concentration of compound amino acids and a bactericidal efficiency, and understand its optimal bactericidal concentration, at a fixed concentration of cefazolin (80 μg/mL for *Escherichia coli* sensitive bacteria K12, and 1,000 μg/mL for *Escherichia coli* cefazolin-resistant bacteria), different concentrations of compound amino acids (0-64 mM) were added to act for 6 hours; then, viable bacteria were counted, and a survival rate was calculated, a calculation formula is: number of viable bacteria when compound amino acids added with different concentrations/number of viable bacteria when compound amino acids not added x 100%; results are shown in FIG. 4.

It can be seen from the figure that after adding 0, 0.125, 0.5, 2.0, 8.0, 32 and 64 mM compound amino acids, a survival rate of *Escherichia coli* sensitive bacteria K12 is 89.6%, 54.9%, 0.705%, 0.0341%, 0.00301%, 0.00247%, and 0.00104% respectively in a case of 80 μg/mL cefazolin added; a survival rate of *Escherichia coli* cefazolin-resistant bacteria is 92.6%, 71.4%, 20.4%, 0.0211%, 0.0181%, 0.0167% and 0.0146% respectively in a case of 1,000 μg/mL cefazolin added. For cefazolin-sensitive bacteria, when a concentration of compound amino acids is 8 mM, a synergistic bactericidal multiple reaches 29,807 times compared with adding antibiotics alone, and when continuing to increase the amino acid concentration, the bactericidal effect is no longer significantly enhanced; for cefazolin-resistant bacteria, when a concentration of compound amino acids is 2 mM, a synergistic bactericidal multiple reaches 4,396 times compared with adding antibiotics alone, and when continuing to increase the amino acid concentration, the bactericidal effect is no longer significantly enhanced. It can be seen that in order to improve the sensitivity of resistant bacteria to antibiotics, 2 mM for compound amino acids can be used as the optimal synergistic bactericidal concentration.

Figure 5:
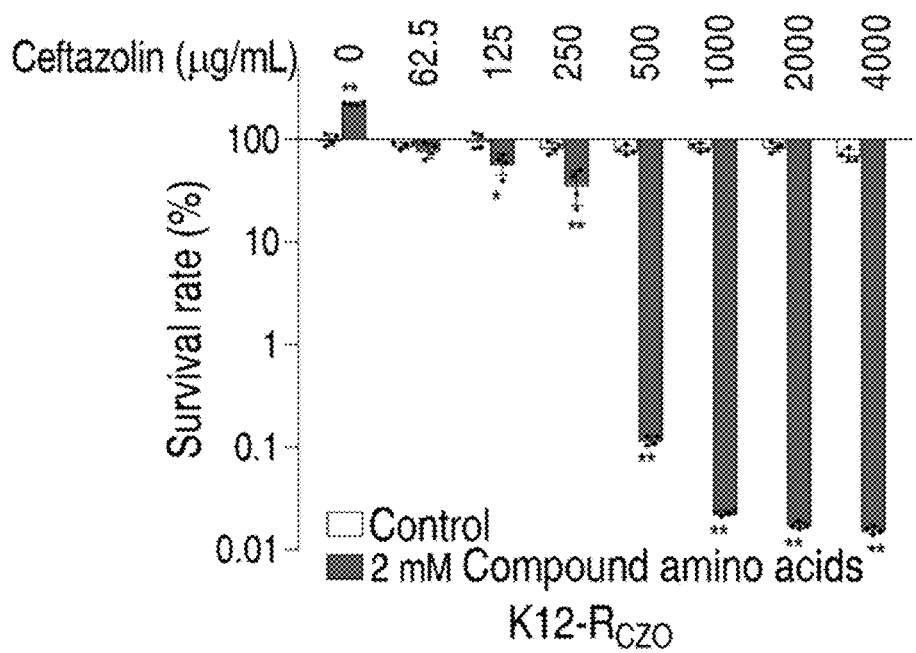
FIG. 5 is a result statistical graph of effects of compound amino acids on improving sensitivity of *Escherichia coli* cefazolin-resistant bacteria to cefazolin with different concentrations in Embodiment 1.

1.2.3.2 Antibiotics Concentration Gradient Effect About Compound Amino Acids Improving Sensitivity of Resistant Bacteria to Cefazolin In order to explore the relationship between compound amino acids improving sensitivity of resistant bacteria to antibiotics and antibiotic concentration, 8 cefazolin concentration gradients (0, 62.5, 125, 250, 500, 1,000, 2,000 and 4,000 μg/mL) were set up; then, 2 mM compound amino acids were added or not added, respectively, after 6 h, plate count method was used to count viable bacteria; under the same antibiotics concentration, survival rates of bacteria when compound amino acids not added (control) and after compound amino acids added were compared. A calculation formula is: number of viable cells when compound amino acids added or not added/number of viable bacteria in M9 after 6 h×100%; results are shown in FIG. 5.

It can be seen from the figure that after 2 mM compound amino acids added, with an increase of the cefazolin concentration, a bactericidal efficiency for resistant bacteria K12-$R_{CZO}$ is greatly improved. Under the cefazolin concentration of 62.5, 125, 250, 500, 1,000, 2,000 and 4,000 μg/mL, when compound amino acids not added, a survival rate of bacteria is as follows: 87.5%, 96.9%, 83.3%, 78.6%, 83.3%, 84.4% and 69.8%, respectively; when compound amino acids added, under the corresponding cefazoline concentration, a survival rate of bacteria is as follows: 78.1%, 57.8%, 35.9%, 0.117%, 0.0228%, 0.0172% and 0.0154%, respectively. After compound amino acids added, an increased bactericidal multiple is 1.12 times, 1.68 times, 2.32 times, 674 times, 3,661 times, 4,909 times and 4,527 times, respectively, and when the cefazolin concentration is increased from 62.5 μg/mL to 2,000 μg/mL, a bactericidal rate is increased from 1.12 times to 4,909 times. These results show that when the cefazolin concentration is within 1000 μg/mL, a promoting bactericidal ability of compound amino acids increases significantly with the increase of antibiotics; at the same time, it can be seen that 1000 μg/mL is the optimal bactericidal concentration of cefazolin against resistant bacteria K12-$R_{CZO}$.

Figure 6:
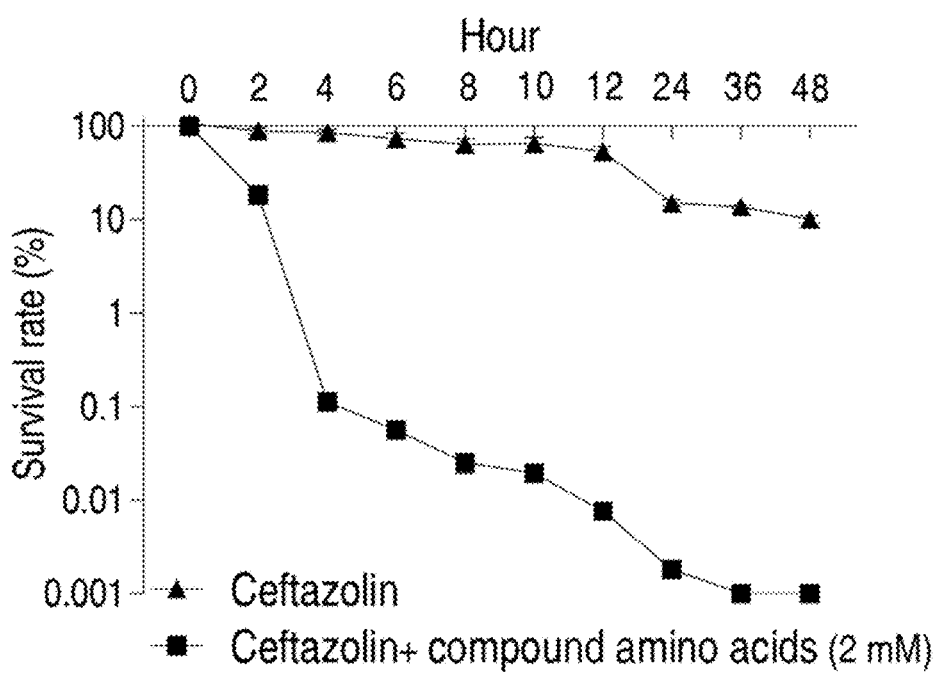
FIG. 6 is a statistical graph of effects of compound amino acids on improving sensitivity of *Escherichia coli* cefazolin-resistant bacteria to cefazolin at different times in Embodiment 1.

1.2.3.3 Time Effect About Compound Amino Acids Improving Sensitivity of Resistant Bacteria to Cefazolin In order to further understand whether effect of compound amino acids improving sensitivity of resistant bacteria to antibiotics has a time effect, in a case of 2 mM compound amino acids and 1000 μg/mL cefazolin added, viable bacteria were counted within 1 to 48 hours, and relationship between bactericidal efficiency and time was observed, results are shown in FIG. 6.

It can be seen from the figure that after adding compound amino acids on the basis of cefazolin added, for cefazolin-resistant bacteria K12-$R_{CZO}$, number of viable bacteria decreases significantly with prolongation of time: from 0, 2, 4, 6, 8, 10, At 12, 24, 36 to 48 h, a survival rate of bacteria is 100%, 18.2%, 0.106%, 0.0563%, 0.0261%, 0.0198%, 0.00716%, 0.00227%, 0.00127% and 0.000208%, respectively; a synergistic bactericidal multiple of compound amino acids is 1 times, 4.97 times, 765.3 times, 1,297.3 times, 2,483.3 times, 3,201.6 times, 6,951.2 times, 6,713.8 times, 10,632.0 times and 50,000.0 times, respectively. The above results show that with prolongation of action time, the survival rate of bacteria continues to decrease. After 4 h, the survival rate of bacteria in synergistic group of compound amino acids is plummeted by two orders of magnitude, and after 6 h and before 10 h, the bacterial survival rate is stable within the same order of magnitude, thus 6 h was chosen as the incubation time for subsequent experiments.

1.2.4 Increase of Content of Intracellular Antibiotics in Bacteria by Compound Amino Acids Bacterial death is related to the number of antibiotics that enter the bacterial cell, and a key reason for drug resistance of bacteria is that the concentration of antibiotics entering the bacterial body is lower than the concentration that makes bacteria dead. Therefore, cefazolin content in bacterial cells after adding compound amino acid was determined.

Figure 7:
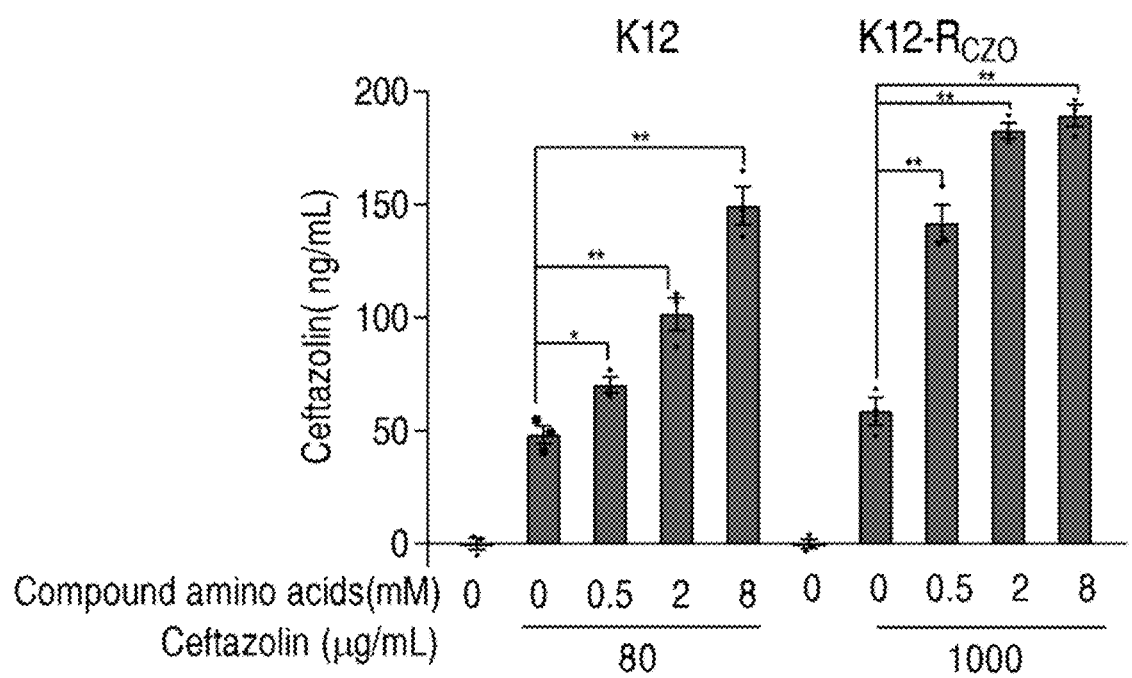
FIG. 7 is a result statistical graph of investigations of compound amino acids increasing of intracellular antibiotic content in bacteria in Embodiment 1.

The prepared bacterial samples were added with 2 mM amino acid compound and cefazolin (80 μg/mL for *Escherichia coli* sensitive bacteria K12, 1,000 μg/mL for *Escherichia coli* cefazolin-resistant bacteria), incubated at 37° C., 200 rpm for 6 h; then bacterial cells were collected by centrifugation, washed twice with normal saline, and adjusted to $OD_{600}$ of bacteria as 0.6; 30 mL of bacterial cells were collected, and after washing, an acetonitrile aqueous solution with a volume ratio of 1:1 was added, and ultrasonically crushed (power 30%, crushed for 2 s, stopped for 3 s, 4 min in total), centrifuged to take a supernatant, repeated the centrifugation to take a supernatant again, filtered with a 0.22 μm filter membrane, and detected by LC/MS, and results are shown in FIG. 7.

After resistant bacterial K12-$R_{CZO}$ was treated with compound amino acids with a concentration of 0, 0.5, 2, 8 mM and 80 μg/mL in synergy with 1000 μg/mL cefazolin, a survival rate of bacteria is 89.6%, 0.705%, 0.0341% and 0.00301%, respectively (results shown in FIG. 4), corresponding intracellular antibiotic content in FIG. 7 is 48.2 ng/mL, 70.2 ng/mL, 101.6 ng/mL and 149.5 ng/mL, respectively.

The above results show that with an increase of concentration of compound amino acids, the intracellular antibiotic content is increased and the survival rate of bacteria is decreased.

Figure 8:
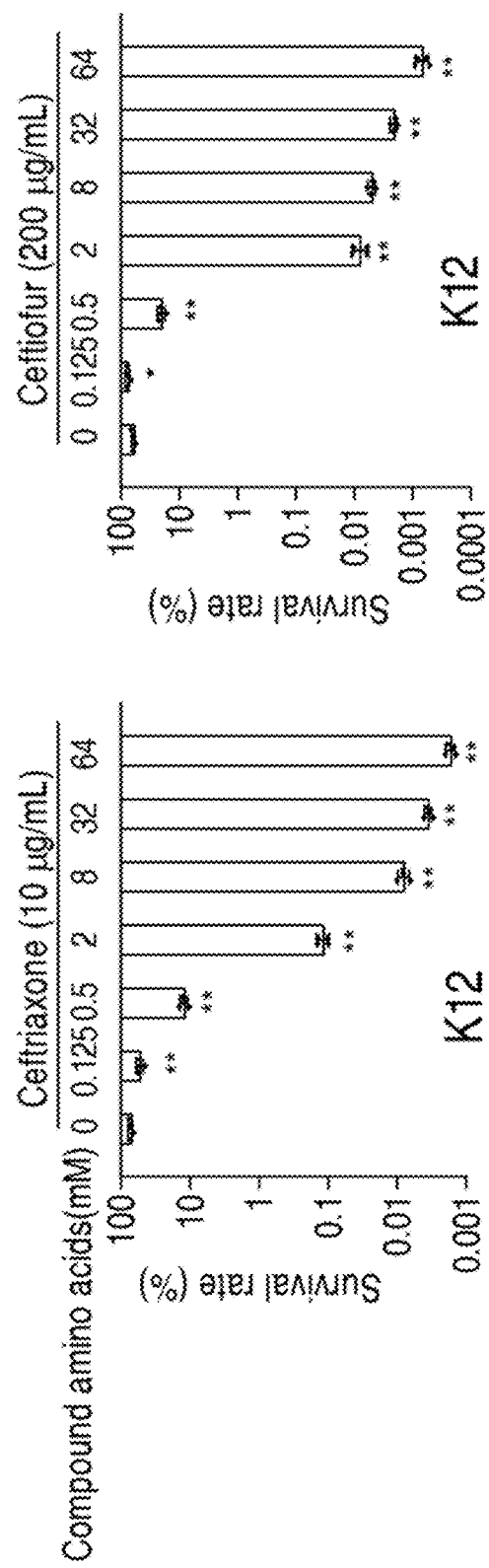
FIG. 8 is a result statistical graph of compound amino acids significantly improving bactericidal efficiency of cephalosporin antibiotics in Embodiment 2.

Embodiment 2 Antibiotics Specificity about Compound Amino Acids Improving Sensitivity of Bacteria to Antibiotics 2.1 Significant Improvement of Bactericidal Efficiency of Cephalosporin Antibiotics It was further studied effects on survival rates of bacteria after adding 0.125, 0.5, 2.0, 8.0, 32, and 64 mM compound amino acids, and after cephalosporin antibiotics (10 μg/mL ceftriaxone, 200 μg/mL ceftiofur) acted on *Escherichia coli* K12 for 6 h; results are shown in FIG. 8.

It can be seen from the figure that after adding 0.125, 0.5, 2.0, 8.0, 32, 64 mM compound amino acids in synergy with ceftriaxone, a survival rate of bacteria is 73.1%, 54.3%, 13.5%, 0.115%, 0.00827%, 0.00345% and 0.00173%, respectively. A survival rate of K12 is decreased by 1.35 times to 42352 times. After synergy with ceftiofur, a survival rate of bacteria is 61.9%, 77.7%, 20.7%, 0.00907%, 0.00589%, 0.00213% and 0.000711%, respectively, and a survival rate of sensitive bacteria K12 is decreased by 0.797 times to 87143 times. These results show that compound amino acids can improve the sensitivity of bacteria to cephalosporin antibiotics.

Figure 9:
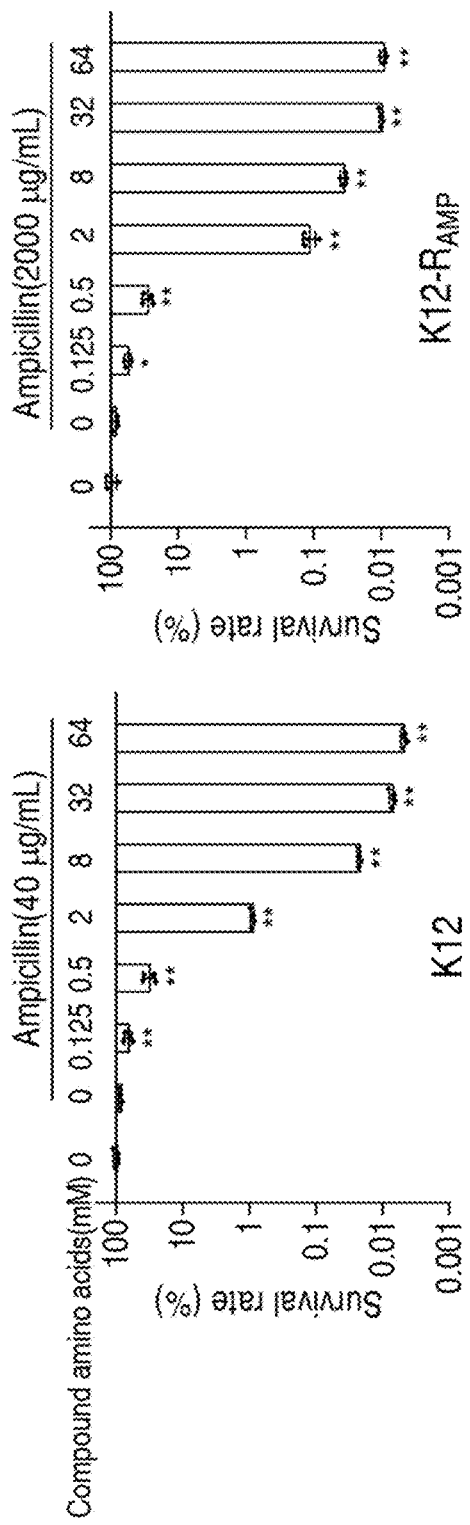
FIG. 9 is a result statistical graph of compound amino acids significantly improving bactericidal efficiency of penicillin antibiotics in Embodiment 2.

2.2 Significant Improvement of Bactericidal Efficiency of Penicillin Antibiotics Taking *Escherichia coli* sensitive bacteria K12 and artificially passaged ampicillin-resistant bacteria (K12-$R_{AMP}$) as research objects, for the former, concentration of ampicillin was 40 µg/mL, and for the latter, concentration of ampicillin was 2000 µg/mL. It was investigated effects of 0.125, 0.5, 2.0, 8.0, 32, and 64 mM compound amino acids in synergy with antibiotics of the above concentrations on survival rates of sensitive bacteria and corresponding resistant bacteria. Results are shown in FIG. 9.

It can be seen from the figure that a survival rate of sensitive bacteria K12 is decreased with an increase of concentration of compound amino acids, a survival rate is 100%, 86.7%, 67.1%, 32.5%, 0.613%, 0.0516%, 0.00722% and 0.00493%, respectively; a survival rate of ampicillin-resistant bacteria (K12-$R_{AMP}$) is 100%, 87.2%, 56.1%, 28.9%, 0.109%, 0.0354%, 0.0101%, and 0.00946%, respectively. After adding compound amino acids, the survival rate of sensitive bacteria K12 is decreased by 1.29 times to 7,578 times, and the survival rate of resistant bacteria K12-$R_{AMP}$ is decreased by 1.55 times to 9,314 times.

2.3 Improvement of Bactericidal Efficiency of Quinolone Antibiotics

Figure 10:
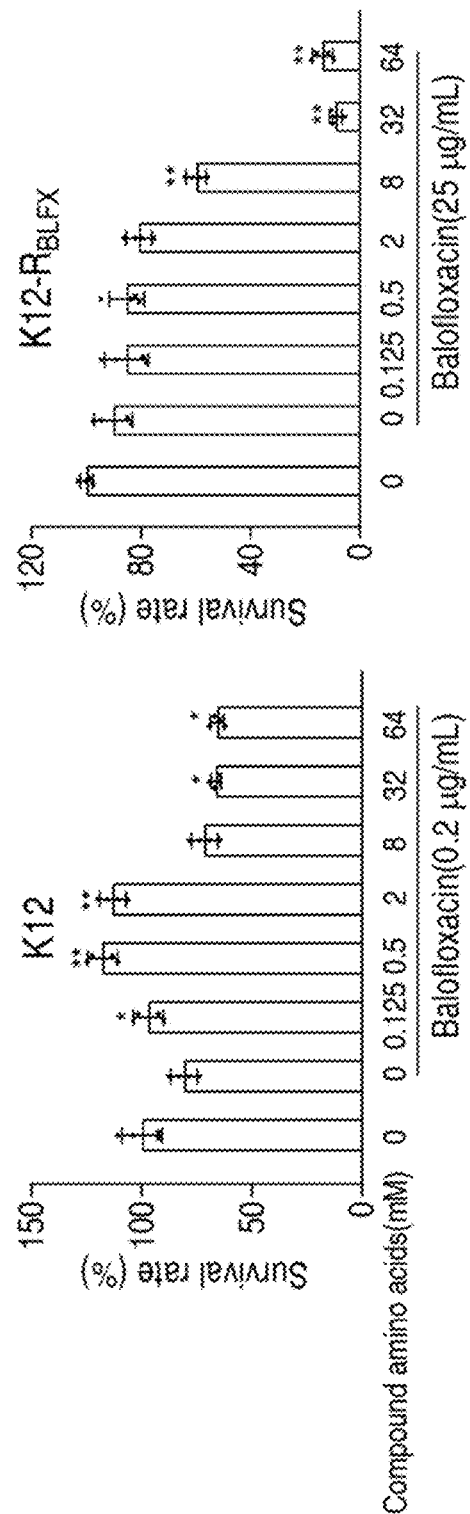
FIG. 10 is a result statistical graph of compound amino acids significantly improving bactericidal efficiency of quinolone antibiotics in Embodiment 2.

Taking *Escherichia coli* sensitive bacteria K12 and balofloxacin-resistant artificially passaged resistant bacteria (K12-$R_{BLFX}$) as research objects, for the former, concentration of balofloxacin was 0.2 µg/mL, and for the latter, concentration of balofloxacin was 25 µg/mL. It was investigated effects of compound amino acids of different concentrations in synergy with antibiotics of the above concentrations on survival rates of sensitive bacteria and corresponding resistant bacteria. Results are shown in FIG. 10.

It can be seen from the figure that 0.125, 0.5, 2.0, 8.0, 32, 64 mM compound amino acids in synergy with balofloxacin resulted in that a survival rate of sensitive bacteria K12 is 100%, 80.9%, 97.1%, 117.9%, 113.3%, 71.7%, respectively, and resulted in that a survival rate of balofloxacin-resistant bacteria (K12-$R_{BLFX}$) is 100%, 90.2%, 85.4%, 85.4%, 80.8%, 59.9%, 10.4% and 13.4%, respectively. Results show that only when the concentration of compound amino acids is greater than 8 mM, there is a certain promoting effect on balofloxacin bactericidation.

2.4 Improvement of Drug Resistance to Aminoglycoside Antibiotics

Figure 11:
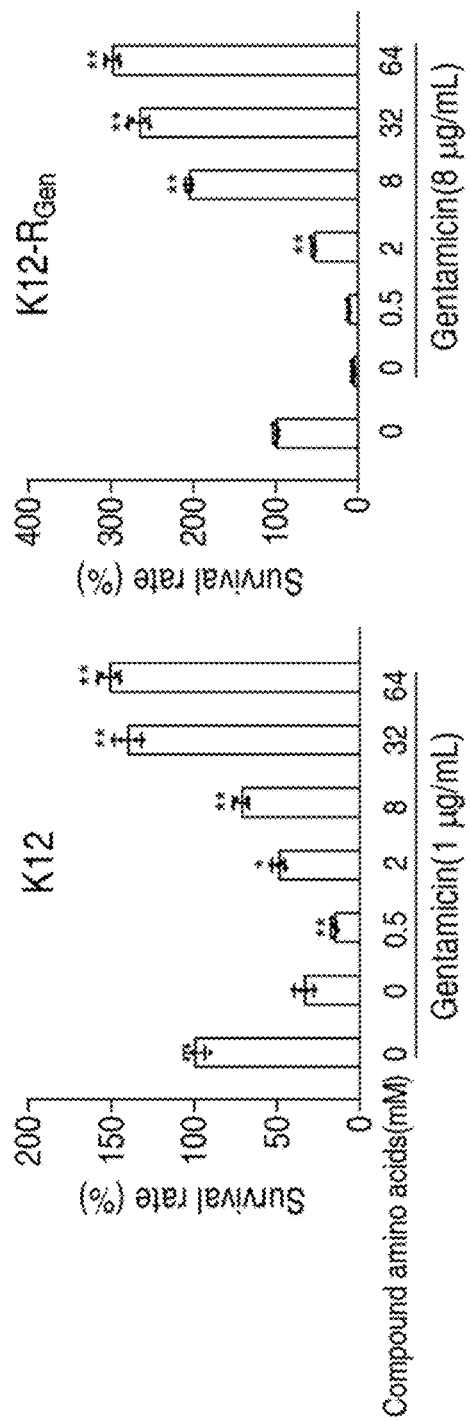
FIG. 11 is a result statistical graph of compound amino acids significantly improving bactericidal efficiency of aminoglycoside antibiotics in Embodiment 2.

Taking *Escherichia coli* sensitive bacteria K12 and artificially passaged gentamicin-resistant bacteria (K12-$R_{Gen}$) as research objects, for the former, concentration of gentamicin was 1 µg/mL, for the latter, concentration of gentamicin was 8 µg/mL. It was investigated effects of compound amino acids of different concentrations in synergy with antibiotics of the above concentrations on survival rates of sensitive bacteria and corresponding resistant bacteria. Results are shown in FIG. 11.

It can be seen from the figure that 0.125, 0.5, 2.0, 8.0, 32, 64 mM compound amino acids in synergy with aminoglycoside antibiotics gentamicin resulted in that a survival rate of sensitive bacteria K12 is 100%, 33.9%, 15.9%, 48.6%, 71.2%, 140.1% and 151.4%, respectively, and resulted in that a survival rate of gentamicin-resistant bacteria (K12-$R_{Gen}$) is 100%, 8.20%, 11.7%, 54.6%, 207.7%, 269.2%, and 302.3%, respectively. Results show that under an action of gentamicin, high concentration of compound amino acids has obvious protective effect on sensitive bacteria and resistant bacteria.

Embodiment 3 Effect of Compound Amino Acids in Synergy with Cefazolin on Survival Rates of Other Species of Bacteria Other Gram-negative bacteria such as *Vibrio alginolyticus, Vibrio parahaemolyticus,* and *Pseudomonas aeruginosa,* and Gram-positive bacteria *Bacillus subtilis* were selected as research objects to investigate bactericidal effect of compound amino acids in synergy with cefazolin; among them, concentration of compound amino acids was 2 mM, concentration of cefazolin was 80 µg/mL, and incubation time was 6 h, a relative survival rate of bacteria was calculated. Results are shown in FIG. 12.

Figure 12:
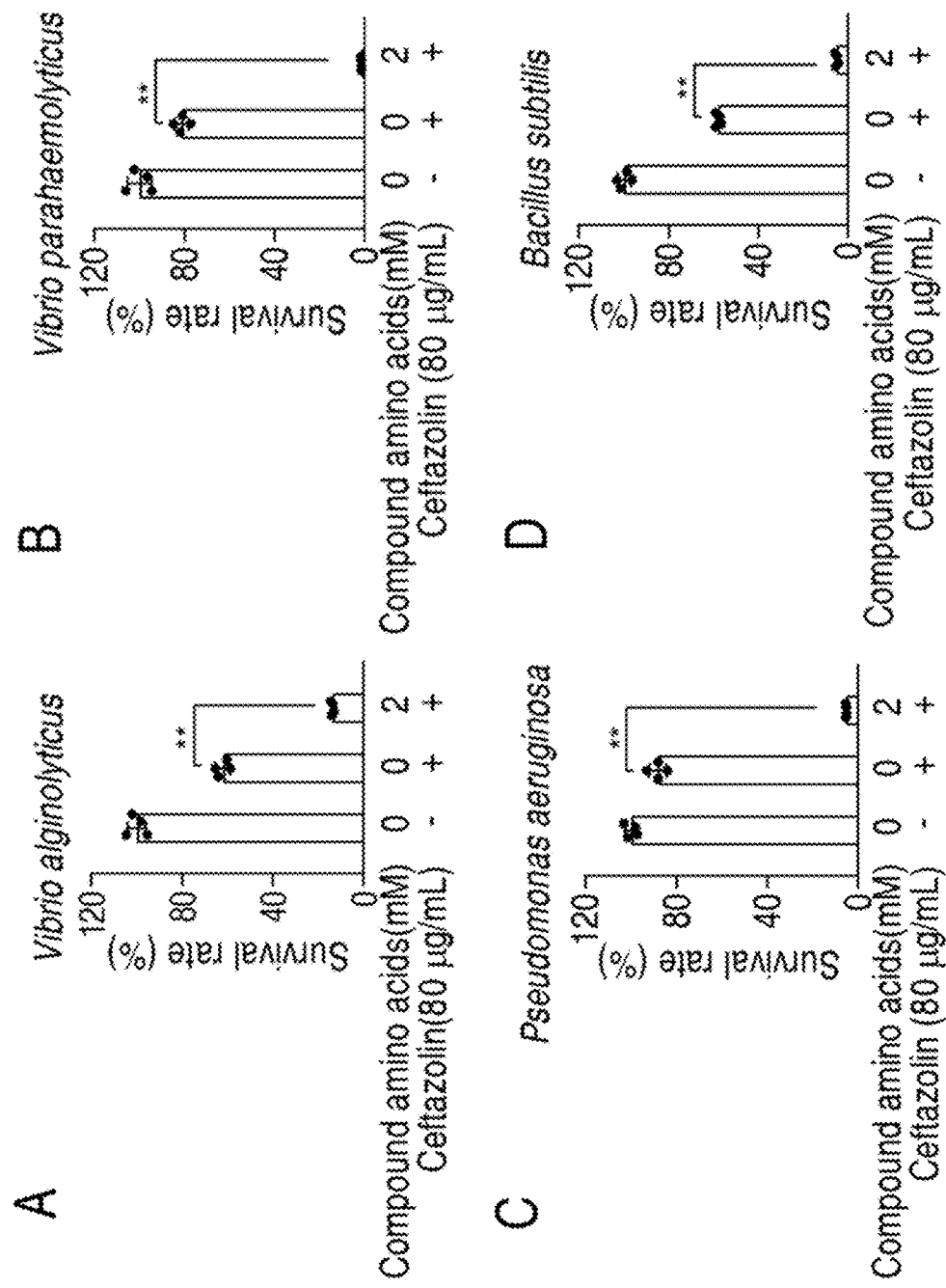
FIG. 12 is a result statistical graph of survival rates of various bacteria against cefazolin after adding compound amino acids in Embodiment 3; A is *Vibrio alginolyticus*, B is *Vibrio parahaemolyticus*, C is *Pseudomonas aeruginosa*, and D is *Bacillus subtilis*.

It can be seen from the figure that after adding 2 mM compound amino acids, cefazolin resulted in that a survival rate of *Vibrio alginolyticus* is decreased from 62.1% to 13.9%, and a synergistic multiple is 4.5 times (A of FIG. 12); a survival rate of *Vibrio parahaemolyticus* is decreased from 79.3% to 1.54%, and a synergistic multiple is 51.6 times (B of FIG. 12); a survival rate of *Pseudomonas aeruginosa* is decreased from 85.9% to 5.4%, and a synergistic multiple is 15.8 times (C of FIG. 12); a survival rate of *Bacillus subtilis* is decreased from 58.0% to 5.1%, and a synergistic multiple is 11.3 times (D of FIG. 12). These results show that a bactericidal effect of compound amino acids in synergy with cefazolin is also effective on other species of bacteria.

Embodiment 4 Improvement of Compound Amino Acids on Sensitivity of Clinical *Escherichia coli* Resistant Bacteria to Cefazolin 4.1 Analysis of Drug Resistance of Clinical *Escherichia coli* Resistant Bacteria Against Cefazolin

*Escherichia coli* (*E. coli*) is one of the most common bacteria in clinical practice. 35 *Escherichia coli* strains clinically obtained were named as Y1 to Y12, Y15 to Y24, Y27, Y28, and Y30 to Y40. The minimum inhibitory concentration (MIC) of these 35 *Escherichia coli* strains clinically obtained against cefazolin antibiotics was detected according to the NCCLS method, at the same time, *Escherichia coli* sensitive bacteria K12 and cefazolin-resistant bacteria K12-$R_{CZO}$ were used as controls to determine the MIC. Measurement results are shown in FIG. 13.

Figure 13:
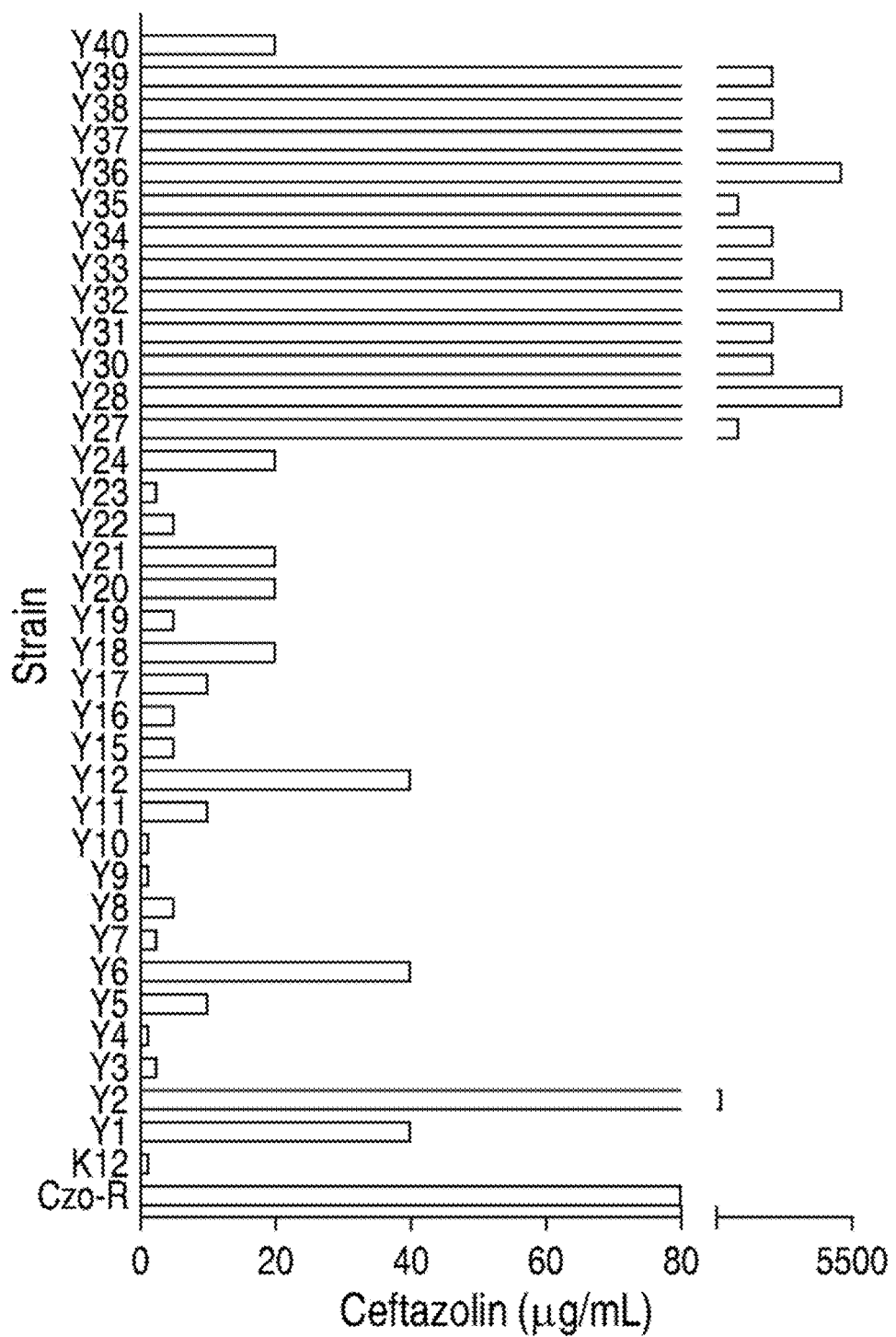
FIG. 13 is a result statistical graph of determination of drug resistance of clinical *Escherichia coli* resistant bacteria against cefazolin in Embodiment 4.

It can be seen from FIG. 13 that MICs of 35 *Escherichia coli* clinical strains were compared with those of *Escherichia coli* sensitive bacteria K12, and 91.4% of the clinical strains has higher MICs than K12 (1.25 µg/mL). Among them, MIC of Y3, Y7 and Y23 is 2.5 µg/mL, MIC of Y8, Y15, Y16, Y19 and Y22 is 5 µg/mL, MIC of Y5, Y11 and Y17 is 10 µg/mL, MIC of Y18, Y20, Y21, Y24 and Y40 is 20 µg/mL, MIC of Y1, Y6 and Y12 is 40 µg/mL, and MICs of 37% of the remaining clinical *Escherichia coli* resistant bacteria are all greater than 640 µg/mL, wherein MIC of Y28, Y32 and Y36 is up to 5120 µg/mL. Results show that among the clinical *Escherichia coli*, for 82.8% of the strains, its MIC is 4 times higher than that of sensitive bacteria, indicating that they are resistant to cefazolin.

Figure 14:
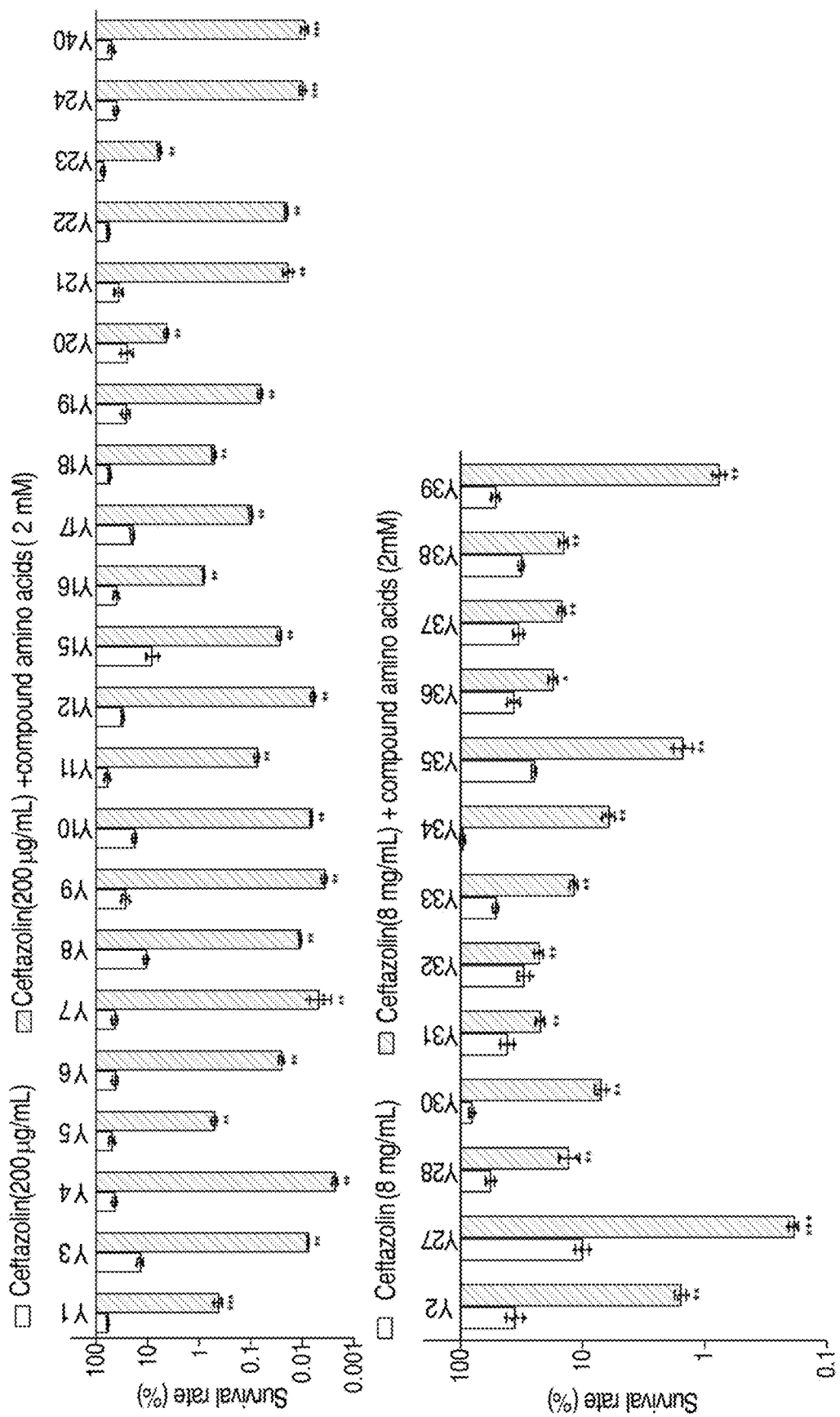
FIG. 14 is a result statistical graph of determination of survival rate of clinical *Escherichia coli* resistant bacteria against cefazolin after adding compound amino acids in Embodiment 4.

4.2 Improvement of Compound Amino Acids on Sensitivity of Clinical Bacteria to Cefazolin Clinical resistant bacteria samples were prepared referring to similar methods in 1.2, 5 ml was dispensed in test tubes, on a basis of 2 mM compound amino acids added, it was incubated with and without addition of cefazolin for 6 hours, then viable bacteria were counted, and a survival rate was calculated; the calculation formula is: number of viable bacteria when antibiotics added/number of viable bacteria when antibiotics not added×100%.; results are shown in FIG. 14.

It can be seen from the figure that when a concentration of cefazolin used is 200 µg/mL, for Y1, Y3, Y4, Y5, Y6, Y7, Y8, Y9, Y10, Y11, Y12, Y13, Y15, Y16, Y17, Y18, Y19, Y20, Y21, Y23, Y24, and Y40 strains with lower MICs, a bactericidal multiple improved by compound amino acids is 138.6 times, 1,881.7 times, 16,521.7 times, 91.3 times, 1,326.9 times, 13,700 times, 1,182.8 times, 5,128.2 times, 3,043.5 times, 723 times, 2,547.1 times, 284.7 times, 48.1 times, 166.7 times, 108.3 times, 337.4 times, 4.6 times, 1,867.5 times, 3,176.5 times, 16.3 times, 3,331.0 times and 5,444.4 times, respectively.

When the concentration of cefazolin used is 8,000 µg/mL, for Y2, Y27, Y28, Y30, Y31, Y32, Y33, Y34, Y35, Y36, Y37, Y38, and Y39 strains with higher MICs, a bactericidal multiple improved by compound amino acids is 23.1 times, 57.7 times, 4.2 times, 11.2 times, 1.7 times, 1.5 times, 4.4 times, 15.7 times, 16.4 times, 2.2 times, 2.1 times, 2.1 times and 68.3 times, respectively.

The above results show that compound amino acids can effectively restore the sensitivity of clinical resistant *Escherichia coli* to cefazolin, and the multiple is related to the degree of drug resistance of the bacteria itself.

Figure 15:
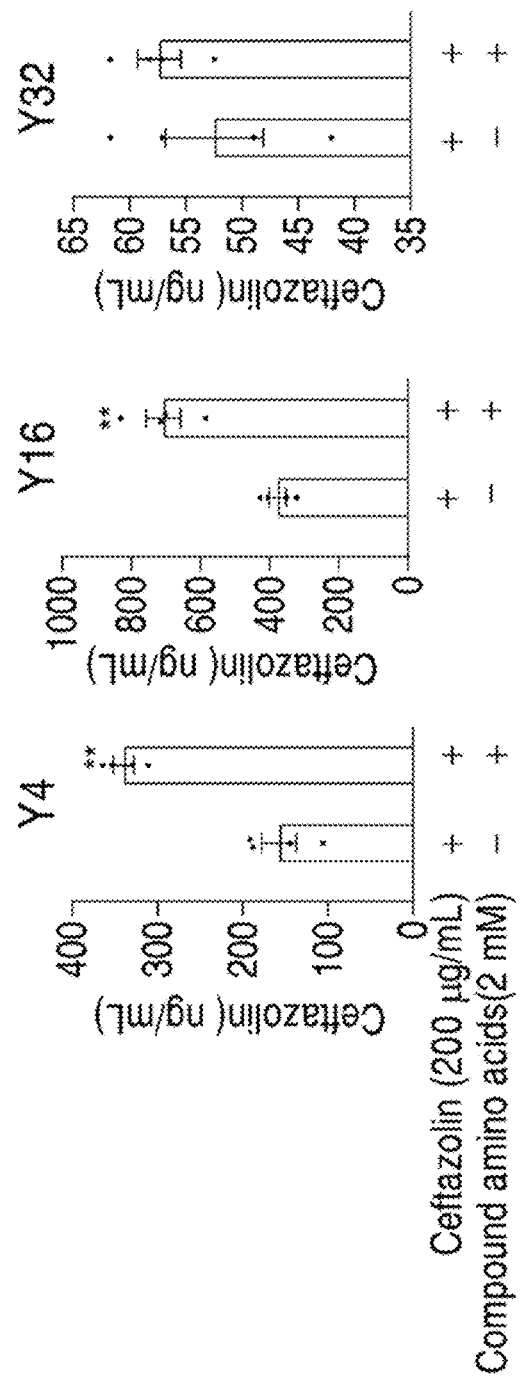
FIG. 15 is a result statistical chart of determination of content of intracellular cefazolin in clinical *Escherichia coli* resistant bacteria after adding compound amino acids in Embodiment 4.

4.3 Improvement of Compound Amino Acids on Intracellular Antibiotic Content of Clinical Resistant Bacteria The antibiotic content in Y4, 16 and Y32 bacteria was determined by the method of 1.2.4, and results are shown in FIG. 15.

It can be seen from the figure that after adding compound amino acids, an antibiotic content of Y4 is increased from 157.4 ng/mL to 339.8 ng/mL, and an intracellular antibiotic content is increased by 182.4 ng/mL; an antibiotic content of Y16 is increased from 377.2 ng/mL to 708.7 ng/mL, an intracellular antibiotic content is increased by 331.5 ng/mL; an antibiotic content of Y32 is increased from 52.5 ng/mL to 57.4 ng/mL, and an intracellular antibiotic content is increased by 4.9 ng/mL.

Figure 16:
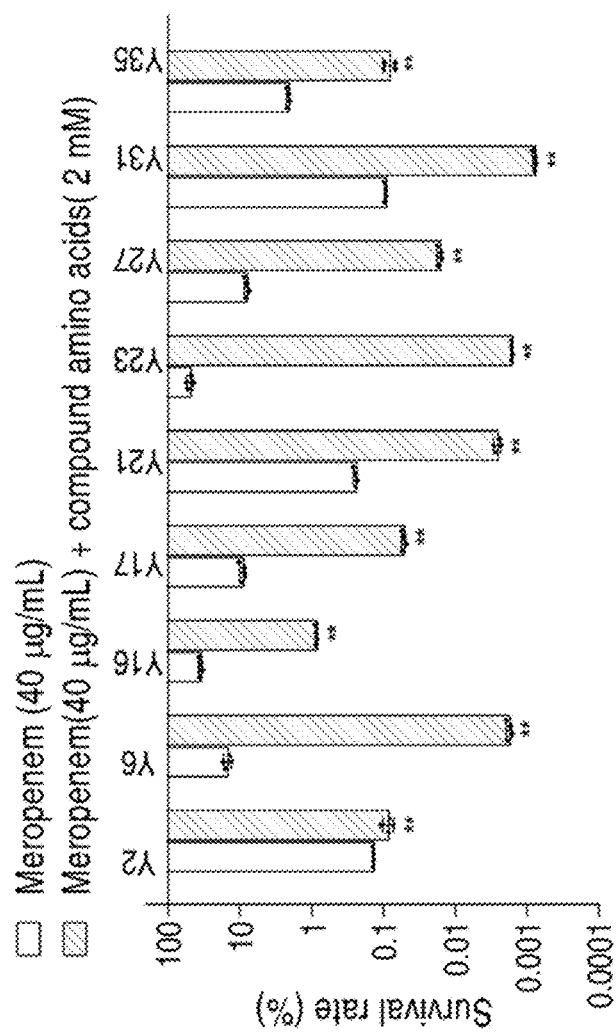
FIG. 16 is a result statistical graph of determination of survival rate of clinical *Escherichia coli* resistant bacteria against meropenem after adding compound amino acids in Embodiment 4.

4.4 Improvement of Compound Amino Acids on Sensitivity of Clinical Bacteria to Other Antibiotics 4.4.1 Improvement on Sensitivity of Clinical Bacteria to Meropenem Nine clinical strains including Y2, Y6, Y16, Y17, Y21, Y23, Y27, Y31, Y35 were randomly selected as research objects, and treated with 2 mM compound amino acids and 40 µg/mL meropenem. Results are shown in FIG. 16.

It can be seen from the figure that a bactericidal multiple with compound amino acids in synergy with antibiotic is 1.6 times, 8,085.7 times, 41.0 times, 175.5 times, 88.2 times, 30384.6 times, 485 times, 120.0 times and 25.9 times, respectively.

4.4.2 Improvement on Sensitivity of Clinical Bacteria to Quinolone Levofloxacin

Figure 17:
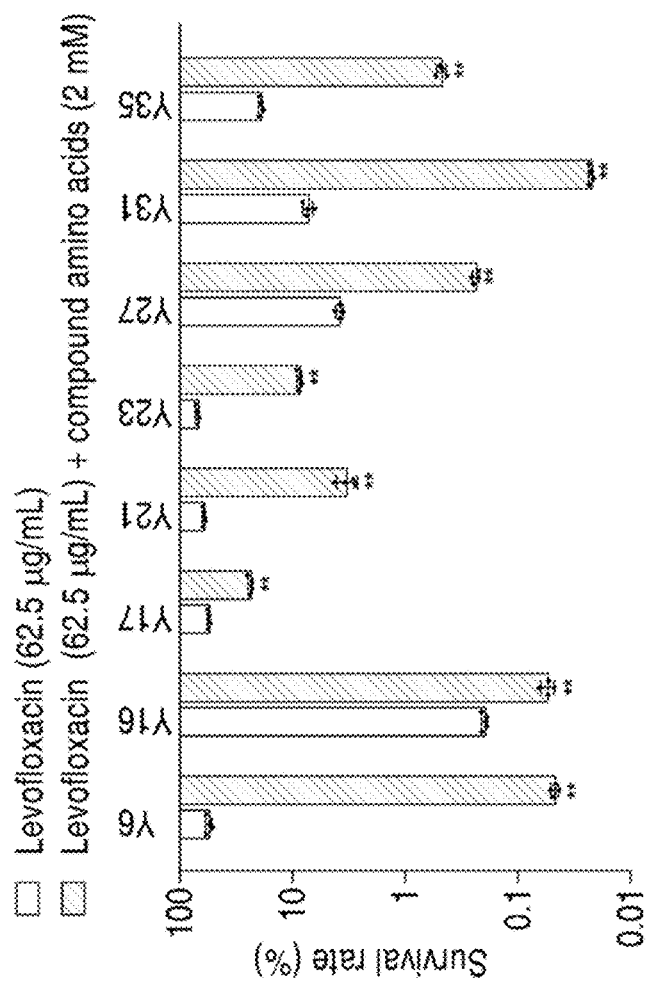
FIG. 17 is a result statistical graph of determination of survival rate of clinical *Escherichia coli* resistant bacteria against levofloxacin after adding compound amino acids in Embodiment 4.

Eight clinical strains including Y6, Y16, Y17, Y21, Y23, Y27, Y31 and Y35 were selected as research objects, and treated with 2 mM compound amino acid and 62.5 µg/mL levofloxacin. Results are shown in FIG. 17.

It can be seen from the figure that a bactericidal multiple with compound amino acids in synergy with antibiotic is 1,226.7 times, 3.6 times, 2.3 times, 19.3 times, 8.3 times, 16.0 times, 326.7 times and 39.5 times, respectively.

Figure 18:
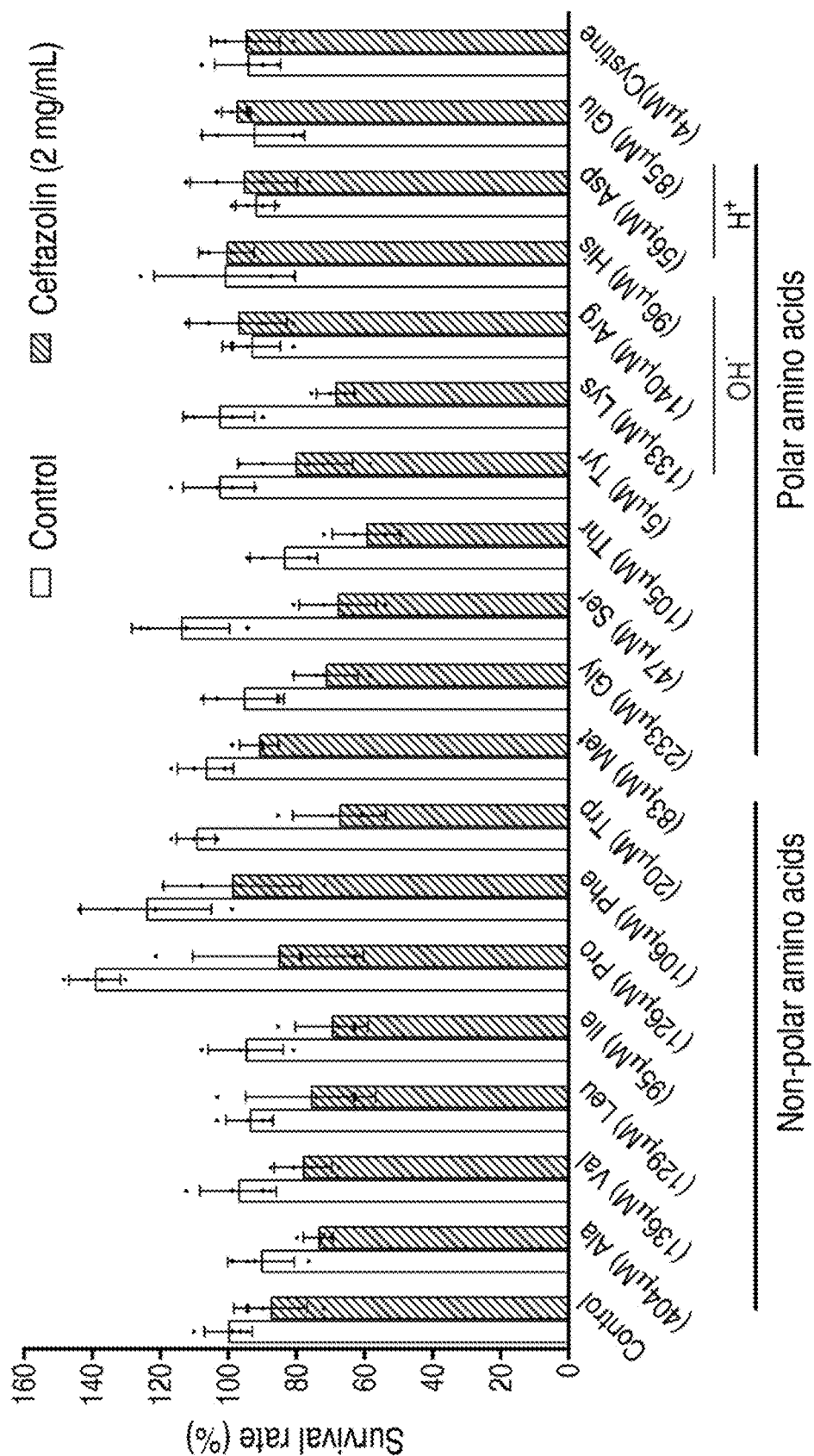
FIG. 18 is a result statistical graph of determination of survival rate of clinical *Escherichia coli* resistant bacteria against cefazolin when adding single amino acid in composition of compound amino acids in Embodiment 5.

Embodiment 5 Effect of Compound Amino Acid Component on Survival Rate of *Escherichia coli* Cefazolin-Resistant Bacteria 5.1 Study on Improvement of Single Amino Acid Component on Sensitivity of *Escherichia coli* Cefazolin-resistant Bacteria to Cefazolin Each amino acid in 2 mM compound amino acids was added alone with a corresponding concentration, and through survival rate of bacteria, it was studied improvement on sensitivity of bacteria to antibiotics when each amino acid was in synergy with cefazolin. Results are shown in FIG. 18.

It can be seen from the figure that a survival rate of bacteria is 85.04% when only cefazolin is added, and when each of the 18 amino acids is added separately with a corresponding molar concentration, a survival rate is: alanine 404 µM (73.6%), valine 136 µM (78.8%), leucine 129 µM (75.7%), isoleucine 95 µM (69.6%), proline 126 µM (85.4%), phenylalanine 106 µM (98.8%), tryptophan 20 µM (67.4%), methionine 83 µM (91.5%), glycine 233 µM (71.4%), serine 47 µM (67.9%), threonine 105 µM (59.4%), tyrosine 5 µM (80.5%), lysine acetate 133 µM (68.6%), arginine 140 µM (97.3%), histidine 96 µM (97.6%), aspartate 56 µM (94.5%), glutamic acid 85 µM (94.5%) and cystine 4 µM (94.1%), respectively. Compared with adding cefazolin antibiotics only, adding alone any one of the 18 amino acids does not have any significant difference from the control group of adding cefazolin only. These results suggest that an amino acid used alone cannot increase sensitivity of bacteria to antibiotics.

Figure 19:
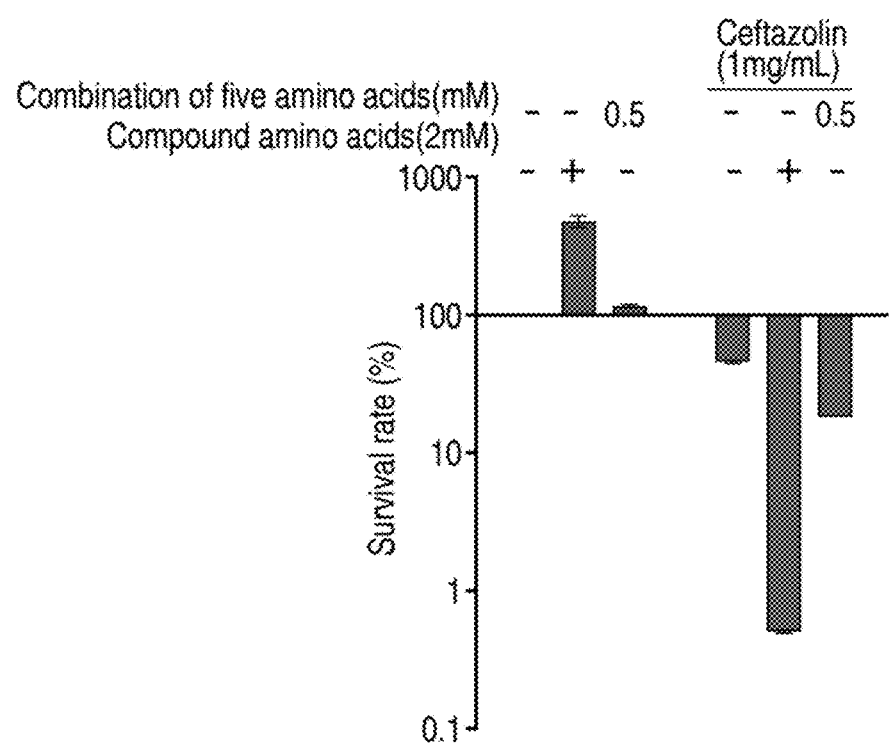
FIG. 19 is a result statistical graph of determination of survival rate of clinical *Escherichia coli* resistant bacteria against cefazolin when adding a combination of five amino acids in composition of compound amino acids in Embodiment 5.

5.2 Study on Improvement of Amino Acid Combination on Sensitivity of *Escherichia coli* Cefazolin-Resistant Bacteria to Cefazolin A combination of five amino acids with a better effect among the above 18 amino acids were selected: glycine 233 µM (71.4%), serine 47 µM (67.9%), tryptophan 20 µM (67.4%), lysine acetate 133 µM (68.6%) and threonine 105 µM (59.4%), to explore the effect of their combined use on bactericidal effect of cefazolin. A total concentration of these five amino acids was about 0.5 mM, which was used in synergy with 1 mg/mL cefazolin to treat cefazolin-resistant bacteria for 6 h, and a survival rate of bacteria was calculated; results are shown in FIG. 19.

It can be seen from the figure that a survival rate of bacteria for M9 control group with antibiotics added is 45.9%; a survival rate of bacteria for compound amino acid group after synergized with antibiotics is 0.001%, and a survival rate of bacteria for 5 amino acid combination group after synergized with antibiotics is 0.15%, a synergistic multiple is 148 times lower than that of the compound amino acid group. These results show that even combination of the 5 amino acids which have a better effect, a synergistic effect to antibiotics is significantly lower than that of the 18 amino acids.

The above-mentioned embodiments are preferred embodiments of the present invention, but implementations of the present invention are not limited by the above-mentioned embodiments, and any other changes, modifications, substitutions, combinations, and simplifications should be equivalent replacement manners, which are all included in the protection scope of the present invention.

What is claimed is:

1. A method of preparing a medicament for improving sensitivity of bacteria to an antibiotic(s), comprising combining i) a compound of amino acids with ii) an antibiotic,
    wherein in the compound of amino acids, a molar concentration ratio of each amino acid to total amino acids is aspartic acid 2.65%-2.8%, glutamic acid 4.09%-4.23%, serine 2.37%-4.64%, histidine 4.62%-4.81%, glycine 11.25%-11.6%, threonine 5.06%-5.22%, alanine 19.57%-20.11%, arginine 6.88%-7%, tyrosine 0.16%-0.27%, cystine 0.09%-0.21%, valine 6.67%-6.8%, methionine 4.04%-4.17%, tryptophan 0.98%-1.04%, phenylalanine 5.12%-5.27%, isoleucine 4.59%-4.74%, leucine 6.44%-6.45%, lysine acetate 6.59%-6.64%, and proline 6.23%-6.32%;
    wherein a total amino acid content of the compound of amino acids within the medicament is 5%-12%;

wherein the antibiotic is selected from a β-lactam antibiotic, a quinolone antibiotic, an aminoglycoside antibiotic, or a combination thereof; and wherein the bacteria is selected from *Escherichia coli, Vibrio alginolyticus, Vibrio parahaemolyticus, Pseudomonas aeruginosa*, and *Bacillus subtilis*.

2. A medicament for improving sensitivity of bacteria to an antibiotic(s), wherein the medicament contains an effective amount of i) a compound of amino acids and ii) an antibiotic, wherein in the compound of amino acids, a molar concentration ratio of each amino acid to total amino acids is aspartic acid 2.65%-2.8%, glutamic acid 4.09%-4.23%, serine 2.37%-4.64%, histidine 4.62%-4.81%, glycine 11.25%-11.6%, threonine 5.06%-5.22%, alanine 19.57%-20.11%, arginine 6.88%-7%, tyrosine 0.16%-0.27%, cystine 0.09%-0.21%, valine 6.67%-6.8%, methionine 4.04%-4.17%, tryptophan 0.98%-1.04%, phenylalanine 5.12%-5.27%, isoleucine 4.59%-4.74%, leucine 6.44%-6.45%, lysine acetate 6.59%-6.64%, and proline 6.23%-6.32%;

wherein a total amino acid content of the compound of amino acids within the medicament is 5%-12%;

wherein the antibiotic is selected from a β-lactam antibiotic, a quinolone antibiotic, an aminoglycoside antibiotic, or a combination thereof; and wherein the bacteria is selected from *Escherichia coli, Vibrio alginolyticus, Vibrio parahaemolyticus, Pseudomonas aeruginosa*, and *Bacillus subtilis*.

3. The medicament according to claim 2, wherein a mass ratio of the antibiotic to total amino acids in the compound amino acids is 1:12.5 to 1:1824.

4. A method of improving sensitivity of a bacteria to an antibiotic(s), comprising administering to the bacteria the medicament of claim 2, and wherein the bacteria is selected from *Escherichia coli, Vibrio alginolyticus, Vibrio parahaemolyticus, Pseudomonas aeruginosa*, and *Bacillus subtilis*.

* * * * *